(12) United States Patent
Wass

(10) Patent No.: US 7,022,788 B2
(45) Date of Patent: Apr. 4, 2006

(54) POLYMERIZATION PROCESS CATALYZED BY A BIDENTATE BISPHOSPHINE-GROUP VIII METAL COMPLEX

(75) Inventor: Duncan Frank Wass, London (GB)

(73) Assignee: BP Chemicals Limited, London (GB)

( * ) Notice: Subject to any disclaimer, the term of this patent is extended or adjusted under 35 U.S.C. 154(b) by 403 days.

(21) Appl. No.: 10/062,673

(22) Filed: Feb. 5, 2002

(65) Prior Publication Data

US 2003/0018141 A1    Jan. 23, 2003

Related U.S. Application Data

(63) Continuation of application No. PCT/GB00/02734, filed on Jul. 17, 2000.

(30) Foreign Application Priority Data

Aug. 6, 1999    (GB) .................................. 9918635

(51) Int. Cl.
C08F 4/26    (2006.01)
C08F 4/70    (2006.01)
(52) U.S. Cl. .................. 526/172; 526/169.1; 526/161; 526/348; 526/318; 526/328; 526/329.3; 526/329.7
(58) Field of Classification Search ................ 526/171, 526/172, 169, 10.1, 526, 161
See application file for complete search history.

(56) References Cited

U.S. PATENT DOCUMENTS 5,010,172 A * 4/1991 Van Leeuwen et al. ..... 528/392
5,137,858 A * 8/1992 van Leeuwen et al. ..... 502/162
5,434,243 A * 7/1995 Mastenbroek et al. ...... 528/392
5,770,684 A * 6/1998 Stewart et al. .............. 528/392

FOREIGN PATENT DOCUMENTS

| EP | 0 702 045 A2 | 3/1996 |
| WO | 97/37765 | 10/1997 |
| WO | WO 97/37765 A1 * | 10/1997 |
| WO | 98/47934 | 10/1998 |
| WO | 98/56839 | 12/1998 |

OTHER PUBLICATIONS

Hawley's Chemical Cictionary, 14$^{th}$ Ed. John Wiley & Sons, Inc., 2001, p. 817.*

* cited by examiner

Primary Examiner—David W. Wu
Assistant Examiner—Rip A. Lee
(74) Attorney, Agent, or Firm—Finnegan, Henderson, Farabow, Garrett and Dunner, L.L.P.

(57) ABSTRACT

A process for the polymerization and copolymerization of olefins is disclosed, comprising contacting the monomeric olefin under polymerization conditions with a polymerization catalyst or catalyst system which comprises (a) a source of a Group VIII metal; (b) a bidentate phosphine ligand having the formula $(R^1)(R^1)P—X—P(R^1)(R^1)$, where each $R^1$ is independently selected from a phenyl group or a substitued phenyl group with the proviso that at least one of the $R^1$ groups is a phenyl group having at least one ortho substituent, and X is a bridging group of the structure $—[N]_x—[P]_y—[N]—$ where x and y are independently 0 or 1, or $—C(R^4)_2—$ where $R^4$ may be the same or different and is hydrogen or a monovavlent hydrocarbyl, substituted hydrocarbyl or hetero-hydrocarbyl group; and optionally (c) a promoter.

23 Claims, No Drawings

POLYMERIZATION PROCESS CATALYZED BY A BIDENTATE BISPHOSPHINE-GROUP VIII METAL COMPLEX

RELATED APPLICATION

This application is a continuation of International Application No. PCT/GB00/02734, filed Jul. 17, 2000.

The present invention relates to a process for the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

EP 850105A discloses that certain bidentate phosphine compounds based on a Group VIII metal are useful catalysts in the polymerisation of linear alternating copolymers of olefins and carbon monoxide (polyketones).

Riehl, ACS Abstracts 1994, Vol 208 (part 1), 530-INOR., discloses oligomerisation of ethylene using as catalyst a nickel salt of 1,2-bis(diisopropylphosphino)ethane.

EP 569032A discloses dimerisation of lower α-olefins using as catalyst a nickel salt of bisdiphenylphosphinomethane.

WO 96/37522 and WO 96/37523 both disclose catalysts for olefin polymerisation comprising a Group VIII metal salt, a promoter and a bidentate phosphine ligand whose substituents may be phenyl or substituted phenyl. The highest activity shown in the Examples can be calculated as less than 1 g/mmol.h.bar. No ortho-substituted phenyl substituents are disclosed.

We have now discovered that certain bidentate phosphine compounds having at least one phenyl substituent which has at least one ortho substituent are surprisingly active catalysts for the polymerisation of olefins.

Accordingly the present invention provides a process for the polymerisation and copolymerisation of olefins, comprising contacting the monomeric olefin under polymerisation conditions with a polymerisation catalyst or catalyst system which comprises (a) a source of a Group VIII metal;

(b) a bidentate phosphine ligand having the formula $(R^1)(R^1)P-X-P(R^1)(R^1)$, where each $R^1$ is independently selected from a phenyl group or a substituted phenyl group, with the proviso that at least one of the $R^1$ groups is a phenyl group having at least one ortho substituent, and X is a bridging group of the structure $-[N]_x-[P]_y-[N]-$ where x and y are independently 0 or 1, or $-C(R^4)_2-$ where each $R^4$ may be the same or different and is hydrogen or a monovalent hydrocarbyl, substituted hydrocarbyl or heterohydrocarbyl group; and optionally (c) a promoter.

A preferred process comprises the steps of:

a) preparing a prepolymer-based catalyst by contacting one or more 1-olefins with a catalyst system, and b) contacting the prepolymer-based catalyst with one or more 1-olefins, wherein the catalyst system is as defined above.

The present invention also encompasses in another aspect the use of a catalyst system as defined above for the polymerisation of 1-olefins.

In the text hereinbelow, the term "catalyst" is intended to include "catalyst system" as defined previously and also "prepolymer-based catalyst" as defined above.

The polymerisation conditions can be, for example, solution phase, slurry phase, gas phase or bulk phase, with polymerisation temperatures ranging from −100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are hydrocarbon olefins, for example, ethylene, $C_{2-20}$ α-olefins, internal olefins, cyclic olefins and dienes, such as propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, styrene, 2-butene, cyclohexene, norbornene, butadiene and 1,5-hexadiene. Other monomers include olefins which comprise an olefin and a polar functionality, eg. methyl methacrylate, methyl acrylate, butyl acrylate, acrylonitrile, vinyl acetate, 2-vinyl-1,3-dioxolane, methyl 3-butenoate, methyl 4-pentenoate, ω-undecylenyl alcohol, ethyl undecylenate, undecylenoic acid, functionalised norbornenes and the like. Preferred monomers for homopolymerisation processes are ethylene and propylene.

The catalysts and process of the invention can also be used for copolymerising ethylene or propylene with each other or with other olefins listed above but particularly 1-butene, 1-hexene, 4-methylpentene-1, 1-octene, methyl methacrylate, methyl acrylate, butyl acrylate, acrylonitrile, vinyl acetate, styrene, methyl 4-pentenoate, ω-undecylenyl alcohol, ethyl undecylenate, undecylenoic acid and functionalised norbornenes.

The catalyst system described above is prepared by reacting together (a) a source of Group VIII metal, (b) a bidentate phosphine ligand having the formula as shown above, and optionally (c) a promoter. These components may be added together simultaneously or sequentially in any order in the presence or absence of monomer(s).

As regards component (a), this is a Group VIII metal; the Group VIII metals are iron, cobalt, nickel, ruthenium, rhodium, palladium, osmium, iridium and platinum. Iron, cobalt, nickel and palladium are preferred; particularly preferred is nickel and palladium; more particularly preferred is nickel.

Component (a), which is the source of the Group VIII metal, can include simple inorganic and organic salts, eg halides, nitrates, carboxylates, acetyl acetonates and the like as well as organometallic and coordination complexes, eg. nickel bis(1,5-cyclooctadiene), allyl nickel halide dimer, 1,2-dimethoxyethane nickel dibromide and (1,5-cyclooctadiene)palladium methylchloride.

As regards component (b), this is a bidentate phosphine ligand having at least two phosphorus atoms joined by a bridging group X which has the structure

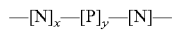
—[N]$_x$—[P]$_y$—[N]— where each of the N atoms which may constitute part or all of the bridge between the said two phosphorus atoms are trivalent and the P atom that may constitute part of the bridge between the said two phosphorus atoms (i.e. y=1) is trivalent or pentavalent. Where all the atoms in the bridge, whether N or P, are trivalent, two of the three bonds of each of the atoms that constitute the bridge are directed to adjacent atoms. The third bond can be directed to an adjacent atom in the bridge (to give a double bond in the bridge), but is more likely to be directed to a monovalent, preferably organic, group which is directly bonded to the respective bridge atom but which does not form part of the bridge itself.

Where y=1, the phosphorus atom forming part of the bridge may alternatively be pentavalent in which case two of the bonds are directed to the adjacent atoms to form part of the bridge. The other three bonds can for example be directed to three monovalent groups or preferably to one monovalent group and a double bond for example to oxygen or sulphur.

Thus it will be understood that the structural unit —[N]$_x$—[P]$_y$—[N]— is intended to include structures such as —[N]$_x$=[PR$^3$]$_y$=[N]— or —[N]$_x$=[P]$_y$—[N(R$^2$)]— for example, where R$^2$ and R$^3$ are as defined below. Howevera preferred bridging group —[N]$_x$—[P]$_y$—[N]— is of the formula —(NR$^2$)$_x$—(PR$^3$)$_y$—N(R$^2$)— where each R$^2$ is the same or different and R$^2$ and R$^3$ represent a hydrogen or a monovalent hydrocarbyl group (for example, methyl, ethyl, isopropyl, n-butyl, t-butyl, n-hexyl, cyclohexyl, phenyl, tolyl and the like), substituted hydrocarbyl group (for example, trifluoromethyl, methoxymethyl, anisyl, phenol, and the like) or hetero-hydrocarbyl group (for example, methoxy, phenoxy, dimethylamino, diethylamino, methylphenoxy, methoxyphenoxy and the like), and x and y are independently 0 or 1. In particular component (b) can be a compound of formula (I):

$(R^1)(R^1)P—(NR^2)_x—(PR^3)_y—NR^2—P(R^1)(R^1)$ (I)

where R$^1$, R$^2$, R$^3$ x and y are defined above.

Each R$^1$ is independently selected from a phenyl group or a substituted phenyl group, subject to the proviso that at least one of the R$^1$ groups is a phenyl group having at least on ortho substituent; suitable substituents include, but are not limited to, halide, hydrocarbyl, substituted hydrocarbyl or heterohydrocarbyl. It is preferred that each R$^1$ group is a substituted phenyl group having at least one ortho substituent; preferably this ortho substituent is independently selected from hydrocarbyl groups (for example, methyl, ethyl, isopropyl, tert butyl, phenyl, benzyl and the like) More preferably this ortho substitutent is independently selected from C$_1$ to C$_6$ alkyl groups. In particular, the alkyl substituents may be independently selected from methyl, ethyl, isopropyl and tert-butyl. This ortho substituent may alternatively be a polar substituent such as an alkoxy (for example, methoxy, ethoxy, phenoxy and the like), amido (dimethylamido, diethylamido and the like) or perfluoronated group (for example trifluoromethyl, perfluoroethyl, pentafluorophenyl and the like). The R$^1$ groups may optionally independently be additionally substituted in any ortho, meta and/or para positions. Adjacent substituents on R$^1$ groups may be linked together to form cyclic structures, for example two adjacent substituents, taken together, may be a —C$_4$H$_8$— unit so as to form part of a cyclohexene ring, or may be a —C$_4$H$_4$— unit so as to form part of a benzene ring (and making R$^1$ a naphthylene group); substituents on adjacent R$^1$ groups may also be linked.

R$^2$ is preferably hydrogen or a hydrocarbyl group, more preferably a C$_1$ to C$_6$ alkyl group, for example methyl or ethyl or an aryl group preferably phenyl or substituted phenyl.

R$^3$ is preferably a hydrocarbyl group, heterohydrocarbyl or substituted hydrocarbyl, more preferably a C$_1$ to C$_6$ alkyl group. Alternatively, R$^3$ is an aryl group for example phenyl or substituted phenyl.

As regards x and y, these are independently 0 or 1. Preferably x and y are both 0 in which case component (b) comprises a bidentate phosphine ligand having the formula $(R^1)(R^1)P—N(R^2)—P(R^1)(R^1)$ where R$^1$ and R$^2$ are as defined above.

The ligands can be prepared using procedures known to the man skilled in the art and disclosed in published literature.

Examples of preferred compounds are
(2-methylphenyl)(phenyl)PN(methyl)P(phenyl)$_2$
(2-methylphenyl)$_2$PN(methyl)P(phenyl)$_2$
(2-methylphenyl)(phenyl)PN(methyl)P(2-methylphenyl) (phenyl)
(2-methylphenyl)$_2$PN(methyl)P(2-methylphenyl)$_2$
(2-ethylphenyl)$_2$PN(methyl)P(2-ethylphenyl)$_2$
(2-isopropylphenyl)$_2$PN(methyl)P(2-isopropylphenyl)$_2$
(2,3-dimethylphenyl)$_2$PN(methyl)P(2,3-dimethylphenyl)$_2$
(2,4-dimethylphenyl)$_2$PN(methyl)P(2,4-dimethylphenyl)$_2$
(2,6-dimethylphenyl)$_2$PN(methyl)P(2,6-dimethylphenyl)$_2$
(2-methyl-6-isopropylphenyl)$_2$PN(methyl)P(2-methyl-6-isopropylphenyl)$_2$
(2,6-diisopropylphenyl)$_2$PN(methyl)P(2.6-diisopropylphenyl)$_2$
(2,4,6-trimethylphenyl)$_2$PN(methyl)P(2,4,6-trimethylphenyl)$_2$ (2-tertbutylphenyl)$_2$PN(methyl)P(2-tertbutylphenyl)$_2$
(2-methoxyphenyl)$_2$PN(methyl)P(2-methoxyphenyl)$_2$
(2-trifluoromethylphenyl)$_2$PN(methyl)P(2-trifluoromethylphenyl)$_2$
(2-phenylphenyl)$_2$PN(methyl)P(2-phenylphenyl)$_2$
(1-naphthyl)$_2$PN(methyl)P(1-naphthyl)$_2$
(1,1'-biphenyl)$_2$PN(methyl)P(1,1'-biphenyl)$_2$
(2-isopropylphenyl)$_2$PN(butyl)P(2-isopropylphenyl)$_2$
(2-isopropylphenyl)$_2$PN(phenyl)P(2-isopropylphenyl)$_2$
(2-isopropylphenyl)$_2$PN(methyl)N(methyl)P(2-isopropylphenyl)$_2$
(2-isopropylphenyl)$_2$PN(methyl)P(Ph)N(methyl)P(2-isopropylphenyl)$_2$ Alternatively, component (b) can be a compound of formula (II):

$$(R^1)(R^1)P\text{—}C(R^4)(R^4)\text{—}P(R^1)(R^1) \quad (II)$$

where $R^1$ is as defined above, and each $R^4$ may be the same or different and is hydrogen or a monovalent hydrocarbyl, substituted hydrocarbyl or hetero-hydrocarbyl group.

$R^4$ is preferably hydrogen or a $C_1$ to $C_6$ alkyl group, for example methyl or ethyl or an aryl group, preferably phenyl; particularly preferred is hydrogen. The $R^4$ groups may be linked to form a cyclic structure.

The ligands can be prepared using procedures known to the man skilled in the art and disclosed in published literature.

Examples of preferred compounds are
(2-methylphenyl)(phenyl)PCH$_2$P(phenyl)$_2$
(2-methylphenyl)$_2$PCH$_2$P(phenyl)$_2$
(2-methylphenyl)(phenyl)PCH$_2$P(2-methylphenyl)(phenyl)
(2-methylphenyl)$_2$PCH$_2$P(2-methylphenyl)$_2$
(2-ethylphenyl)$_2$PCH$_2$P(2-ethylphenyl)$_2$
(2-isopropylphenyl)$_2$PCH$_2$P(2-isopropylphenyl)$_2$
(2,3-dimethylphenyl)$_2$PCH$_2$P(2,3-dimethylphenyl)$_2$
(2,4-dimethylphenyl)$_2$PCH$_2$P(2,4-dimethylphenyl)$_2$
(2,6-dimethylphenyl)$_2$PCH$_2$P(2,6-dimethylphenyl)$_2$
(2-methyl-6-isopropylphenyl)$_2$PCH$_2$P(2-methyl-6isopropylphenyl)$_2$
(2,6diisopropylphenyl)$_2$PCH$_2$P(2,6diisopropylphenyl)$_2$
(2,4,6trimethylphenyl)$_2$PCH$_2$P(2,4,6trimethylphenyl)$_2$
(2-tertbutylphenyl)$_2$PCH$_2$P(2-tertbutylphenyl)$_2$
(2-methoxyphenyl)$_2$PCH$_2$P(2-methoxyphenyl)$_2$
(2-trifluoromethylphenyl)$_2$PCH$_2$P(2-trifluoromethylphenyl)$_2$
(2-phenylphenyl)$_2$PCH$_2$P(2-phenylphenyl)$_2$
(1-naphthyl)$_2$PCH$_2$P(1-naphthyl)$_2$
(1,1'-biphenyl)$_2$PCH$_2$P(1,1'-biphenyl)$_2$
(2-isopropylphenyl)$_2$PC(phenyl)$_2$P(2-isopropylphenyl)$_2$
(2-isopropylphenyl)$_2$PC(methyl)$_2$P(2-isopropylphenyl)$_2$ As regards component (c) which is a promoter; this may be any compound which generates an active catalyst with components (a) and (b). Component (c) is suitably selected from, but not limited to, organoaluminium compounds and organoboron compounds. Mixtures of promoter compounds may also be used. Suitable organoaluminium compounds include compounds of the formula AlR$_3$, where each R is independently $C_1$–$C_{12}$ alkyl or halo. Examples include trimethylaluminium (TMA), triethylaluminium (TEA), triisobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof Commercially available alumoxanes are generally believed to be mixtures of linear and cyclic compounds. The cyclic alumoxanes can be represented by the formula [R$^{16}$AlO]$_s$ and the linear alumoxanes by the formula R$^{17}$(R$^{18}$AlO)$_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups. Alkylalumoxanes such as methylalumoxane (MAO) are preferred.

In this context it should be noted that the term "alkylaumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trinethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula AlR$_3$ additional to any AlR$_3$ compound incorporated within the alkylalumoxane when present. When aluminoxanes are employed as promoters it is preferred that they contain fairly low levels of or no free trialkylaluminium compounds.

Examples of suitable organoboron compounds are boroxines, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, H$^+$(OEt$_2$)$_2$[(bis-3,5-trifluoromethyl)phenyl]borate, trityltetra(pentafluorophenyl)borate and tris(pentafluorophenyl)boron.

An alternative class of activators comprise salts of a cationic oxidising agent and a non-coordinating compatible anion. Examples of cationic oxidising agents include: ferrocenium, hydrocarbyl-substituted ferrocenium, Ag$^+$, or Pb$^{2+}$. Examples of non-coordinating compatible anions are BF$_4^-$, SbCl$_6^-$, PF$_6^-$, tetrakis(phenyl)borate and tetrakis(pentafluorophenyl)borate.

In the preparation of the catalysts of the present invention the quantity of activating compound selected from organoaluminium compounds and organoboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of Group VIII metal. In some cases, for certain combinations of component (a) and (b), a promoter (c) may not be required.

In some cases, by suitable choice of metal source, it is possible to utilise a catalyst in which components (a) and (b) are combined in a pre-formed single entity of formula (III) below. Accordingly a further aspect of the invention provides a process for the polymerisation and copolymerisation of olefins, comprising contacting the monomeric olefin under polymerisation conditions with a polymerisation catalyst or catalyst system which comprises (i) a compound of the formula (III)

$$[(L)_p(L^1)_qM^m(Q)](A^n)_{(m-p)/n} \quad (III)$$

and optionally (ii) a promoter,
wherein M is a Group VIII metal in formal oxidation state m, each L is independently a monoanionic group or ligand; $L^1$ is independently a neutral group or ligand; each A is independently a weakly coordinating or non-coordinating anion with a formal negative charge of n; and Q is a bidentate phosphine ligand having the formula $(R^1)(R^1)P$—$X$—$P(R^1)(R^1)$, where each $R^1$ is independently selected from a phenyl group or a substituted phenyl group, with the proviso that at least one of the $R^1$ groups is a phenyl group having at least one ortho substituent, and X is a bridging group of the structure —$[N]_x$—$[P]_y$—$[N]$— where x and y are independently 0 or 1, or —$C(R^4)_2$— where each $R^4$ may be the same or different and is hydrogen or a monovalent hydrocarbyl, substituted hydrocarbyl or hetero-hydrocarbyl group;

p may have any value between 0 and m, and q is an integer between 0 and 4. For example, when m=2 then p may be 0, 1 or 2.

Examples of L are halide, acetate, acetyl acetonate, alky, heteroalkyl, allyl, hydride and the like. Examples of $L^1$ are an olefin, carbon monoxide, a phosphine, a solvent molecule such as water, diethyl ether, acetone, acetonitrile, and the like. Examples of A are $BF_4^-$, $SbF_6^-$, $PF_6^-$, triflate, aryl or alkyl borate, sulfate, phosphate and the like. When M is nickel or palladium, it is preferred that n=1 and preferred values of p, q and m are p=0, q=2 and m=0
p=1, q=1 and m=2
p=2, q=0 and m=2
and p=0, q=2 and m=2

In some cases, the L ligands, $L^1$ ligands or L and $L^1$ ligands may be linked together to form bidentate or multidentate ligands. For some cases, for certain compounds of the above formula, a promoter compound may not be required.

Certain compounds used in the process of the present invention are novel, and accordingly a further aspect of the invention comprises compounds of formula (IV):

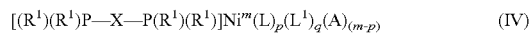

$$[(R^1)(R^1)P\text{—}X\text{—}P(R^1)(R^1)]Ni^m(L)_p(L^1)_q(A)_{(m-p)} \quad (IV)$$

wherein each $R^1$ is independently selected from a phenyl group or a substituted phenyl group with the proviso that at least one of the $R^1$ groups is a phenyl group having at least one ortho substituent; X is a bridging group of the structure —$N(R^2)$ where $R^2$ is a hydrogen or hydrocarbyl group, or —$C(R^4)_2$— where each $R^4$ may be the same or different and is hydrogen or a hydrocarbyl group; m is the formal oxidation state of nickel; each L is independently a monoanionic group or ligand; $L^1$ is independently a neutral group or ligand; each A is independently a weakly coordinating or non-coordinating anion; p is any integer between 0 and m, q is an integer between 0 and 4.

Preferably m=p=0 and q=2; m=p=2 and q=0; or m=2, p=1 and q=1. It is also preferred that L is halide, acetate, acetyl acetonate, alkyl, heteroalkyl, allyl, or hydride; $L^1$ is an olefin, carbon monoxide, a phosphine or a solvent molecule; and A is $BF_4^-$; $SbF_6^-$, $PF_6^-$, triflate, aryl or alkyl borate. Preferably each $R^1$ group is a substituted phenyl group having at least one ortho halide, hydrocarbyl, substituted hydrocarbyl or heterohydrocarbyl substituent. The catalysts utilised in the present invention can if desired comprise more than one of the defined compounds and can also be used in conjunction with one or more other types of catalyst, such as those of the type used in conventional Ziegler-Natta catalyst systems, metallocene-based catalysts, monocyclo-pentadienyl- or constrained geometry based catalysts, heat activated supported chromium oxide catalysts (eg Phillips-type catalyst), nickel and palladium α-diimine catalysts or iron and cobalt pyridyldiimine catalysts.

The catalysts utilised in the present invention can be unsupported or supported on a support material, for example, silica, alumina, $MgCl_2$ or zirconia, or on a polymer or prepolymer, for example polyethylene, polypropylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

Irrespective of the polymerisation or copolymerisation technique employed, polymerisation or copolymerisation may be carried out under conditions that substantially exclude oxygen, water, and other materials that may act as catalyst poisons. However, some catalysts or catalyst systems utilised in the present invention exhibit good tolerance of such potential poisons, and polymerisation or copolymerisation may be carried out in the presence of oxygen, water or other potential poisons. Polymerisation or copolymerisation may also be carried in water as a diluent, either as a solution, suspension or emulsion. Other donor solvents may also be used as diluent, for example alcohols (for example methanol, ethanol, isopropanol), ethers (for example diethyl ether, tetrahydrofuran) and the like. Polymerisation or copolymerisation may also be carried out using crude olefin feedstocks as monomers, which may contain potential poisons.

Also, polymerisation or copolymerisation can be carried out in the presence of additives to control polymer or copolymer molecular weights.

The use of hydrogen gas as a means of controlling the average molecular weight of the polymer or copolymer may apply generally to the polymerisation process of the present invention. For example, hydrogen may be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials. Most preferably the catalyst system is supported on the support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising is, gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

In the polymers made according to the present invention, each polymer chain contains a C═C bond, preferably at its end. This double bond can be useful for further chemical modification. Branched ethylene homopolymers can be prepared by the process of the invention, and the degree of branching controlled.

Depending upon the use of the polymer product, minor amounts of additives are typically incorporated into the polymer formulation such as acid scavengers, antioxidants, stabilizers, peroxides and the like. Generally, these additives are incorporated at levels of about 25 to 2000 ppm, typically from about 50 to about 1000 ppm, and more typically 400 to 1000 ppm, based on the polymer.

Examples of uses for polymer compositions made according to the invention include use to form fibres, extruded films, blown films, tapes, spunbonded webs, moulded or thermoformed products, lubricants, additives and the like.

Fillers such as silica, glass fibers, talc, and the like, nucleating agents, and colourants also may be added to the polymer compositions as known by the art.

The present invention is illustrated in the following Examples.

EXAMPLES

All manipulations were performed under anaerobic conditions unless stated otherwise. Solvents and gases were dried and degassed by standard procedures Chemicals were obtained from commercial suppliers (Aldrich Chemical Co. or Strem Chemicals) unless stated otherwise. Methyl alumoxane and modified methyl alumoxane were obtained from Witco Chemical Co. Silica was obtained from Crossfield. $H^+(OEt_2)_2$tetrakis(bis-3,5-trifluoromethylphenyl)borate was prepared according to literature procedures (Brookhart et al, Organometallics 1992, 11, 3920). Polymer molecular weights were determined by gel permeation chromatography (GPC) using a PL gel 2× mixed bed-D, 30 cm, 5 micron columns, trichlorobenzene eluent and a flow rate of 1.0 mil/min (nominal) at 150° C. using a refractive index detector. Polymer branching levels and comonomer incorporation were determined by $^1H$ and $^{13}C$ NMR spectroscopy using sample solutions in p-xylene-$d_{10}$ 110° C. or $C_2D_2Cl_4$/1,2,4-trichlorobenzene at 130° C.

Example 1

Preparation of (2-isopropylphenyl)$_2$PN(methyl)P(2-isopropylphenyl)

(2-isopropylphenyl)$_2$PN(methyl)P(2-isopropylphenyl) was prepared as follows: 2-isopropylphenylmagnesiumbromide (prepared by treating magnesium turnings (9 g, 0.375 mol) with 2-isopropylbromobenzene (15 g, 0.075 mol) in tetrahydrofuran, in the presence of one crystal of iodine) was added dropwise to a solution of PBr$_3$ (2.9 cm$^3$, 30 mmol) in diethyl ether. The solvent was removed under reduced pressure and P(2-isopropylphenyl)$_2$Br was isolated, without further purification, in 70% yield. NEt$_3$ (10.9 g, 0.1 mol) and NMeH$_2$ (2M solution in tetrahydrofuran, 5.5 cm$^3$, 11 mmol) were then added to the P(2-isopropylphenyl)$_2$Br (22 mmol) in dichloromethane (80 cm$^3$) and the resulting mixture was heated under reflux for 24 hours. The solvent was removed under reduced pressure and the product was isolated as a white solid by repeated washing with methanol. The yield was 40%. $^{31}P\{^1H\}$ NMR (CD$_2$Cl$_2$) δ=57 ppm.

Example 2

Preparation of (2-ethylphenyl)$_2$PN(methyl)P(2-ethylphenyl)

(2-ethylphenyl)$_2$PN(methyl)P(2-ethylphenyl) was prepared by following a similar procedure as described for Example 1 only with the following differences: 2-ethylphenylmagnesiumbromide (prepared by treating magnesium turnings (9 g, 0.375 mol) with 2-ethylbromobenzene (0.075 mol) in tetrahydrofuran, in the presence of one crystal of iodine) was added dropwise to a solution of PBr$_3$ (2.9 cm$^3$, 30 mmol) in diethyl ether. The solvent was removed under reduced pressure and P(2-ethylphenyl)$_2$Br was isolated, without further purification. NEt$_3$ (10.9 g, 0.1 mol) and NMeH$_2$ (2M solution in tetrahydrofuran, 5.5 cm$^3$, 11 mmol) were then added to the P(2-ethylphenyl)$_2$Br (22 mmol) in dichloromethane (80 cm$^3$) and the resulting mixture was stirred at ambient temperature for 24 hours. The solvent was removed under reduced pressure and the product was isolated as a white solid by repeated washing with methanol. The yield was 70%. $^{31}$P{$^1$H} NMR (CD$_2$Cl$_2$) δ=57 ppm.

Example 3

Preparation of (2-methylphenyl)$_2$PN(methyl)P(2-methylphenyl)

(2-methylphenyl)$_2$PN(methyl)P(2-methylphenyl) was prepared by following a similar procedure as described for Example 1 only with the following differences; 2-methylphenylmagnesiumbromide (2M solution in diethyl ether; 40.2 ml, 80.4 mmol) was added dropwise to a solution of PCl$_3$ (3.51 ml, 40.2 mmol) in diethyl ether and the resulting mixture was stirred for a few minutes. The solvent was removed in vacuo and a mixture of P(2-methylphenyl)$_2$Cl and P(2-methylphenyl)$_2$Br was extracted from the residue with toluene and filtered through a celite column. The yield was 80%. First NEt$_3$ (2.73 g, 27 mmol) and then NMeH$_2$ (2M solution in tetrahydrofuran, 2.27 ml, 4.5 mmol) were added to the mixture of P(2-methylphenyl)$_2$Cl and P(2-methylphenyl)$_2$Br (2.64 g, 9 mmol) in dichloromethane (20 ml) and the resulting mixture was stirred at ambient temperature for a few minutes. The solvent was removed in vacuo and the product was isolated as a white solid by repeated washing with methanol The yield was 70%. $^{31}$P{H} NMR (CD$_2$Cl$_2$) δ=58 ppm.

Example 4

Preparation of (2-methoxphenyl)$_2$PN(methyl)P(2-methoxyphenyl)$_2$ (2-methoxyphenyl)$_2$PN(methyl)P(2-methoxyphenyl) was prepared by following a similar procedure as described for Example 1 only with the following differences: 2-methoxyphenylmagnesiumbromide (prepared by treating magnesium turnings (3.7 g, 0.154 mol) with 2-bromoanisole (0.077 mol) in tetrahydrofuran, in the presence of one crystal of iodine) was added dropwise to a solution of PCl$_3$ (3.2 ml, 0.37 mol) in tetrahydrofuran (100 ml) and the solution stirred for a few minutes. The solvent was removed in vacuo and a mixture of P(2-methoxyphenyl)$_2$Cl and P(2-methoxyphenyl)$_2$Br was extracted from the residue with toluene and filtered through a celite column. The yield was 81%. First NEt$_3$ (2.73 g, 27 mmol) and then NMeH$_2$ (2M solution in tetrahydrofuran, 2.27 ml, 4.5 mmol) were added to the mixture of P(2-methoxyphenyl)$_2$Cl and P(2-methoxyphenyl)$_2$Br in tetrahydrofuran (20 ml) and the resulting mixture was stirred under reflux for a five hours. The solvent was removed in vacuo and the product was isolated as a white solid by repeated washing with methanol.

The yield was 60%. $^{31}$P{$^1$H} NMR (CD$_2$Cl$_2$) δ=53 ppm.

Example 5

Preparation of (2,4,6-trimethylphenyl)$_2$PN(methyl)P(2,4,6-trimethylphenyl)$_2$ i) (2,4,6trimethylphenyl)$_2$PBr:

PBr$_3$ (7.5 mmol, 0.7 mL) was dissolved in tetrahydrofuran (20 mL) under a nitrogen atmosphere. The solution was cooled to −78° C. and mesityl magnesium bromide (supplied from Aldrich Chemical Co., 1.0 M in diethyl ether, 15 mmol, 15 mL) was added dropwise keeping the internal temperature below −50° C. The reaction mixture was warmed to room temperature (~20 min) and the solvent was removed in vacuo. Toluene (40 mL) was added to oily residue and the stirred slurry was heated to 90° C. for 1 hour. The toluene supernatent was isolated by filtration and the solvent was removed to provide an off-white gum. $^{31}$P NMR analysis showed the crude product to contain largely a single species (δ=77.5 ppm) which was consistent with the desired bromophosphine compound.

ii) (2,4,6-trimethylphenyl)$_2$PN(methyl)P(2,4,6-trimethylphenyl)$_2$:

The (2,4,6-trimethylphenyl)$_2$PBr compound (crude, prepared as detailed above: 3.75 mmol) was dissolved in dichloromethane (20 mL) and triethylamine (2.8 mL) was added. Methylamine was added dropwise (2 M solution in tetrahydrofuran, 0.76 mL, 1.52 mmol) and the mixture was heated to 40° C. overnight. The solvent was removed in vacuo and methanol (20 mL) was added. The resulting off-white precipitate was isolated by filtration (900 mg, 105%). $^{31}$P NMR analysis of the crude showed evidence for the formation of the desired ligand (δ=62 ppm) in approximately 30% yield. The crude ligand was used in preparation of a nickel bromide complex described in Example 11.

Example 6

Preparation of (2-isopropylphenyl)$_2$PCH$_2$P(2-isopropylphenyl)$_2$ (2-isopropylphenyl)$_2$PCH$_2$P(2-isopropylphenyl)$_2$ was prepared as follows: A solution of Cl$_2$PCH$_2$PCl$_2$ (1.3 g, 6.0 mmol) in tetrahydrofuran (20 cm$^3$) was cooled to a temperature of −78° C. and a solution of 2-isopropylphenyl lithium (32 mmol, which was freshly prepared by addition of n-BuLi to either 2-isopropylbromobenzene or 2-isopropylphenylmagnesiumhalide) in tetrahydrofuran or diethyl ether (20 cm$^3$) was added dropwise. After stirring at a temperature of −78° C. for 60 minutes, the mixture was allowed to warm to ambient temperature and was stirred for a further 2 hours. The solvent was removed under reduced pressure, dichloromethane (100 cm$^3$) and water (60 cm$^3$) were added and the mixture was transferred to a separation funnel. The organic layer was separated, dried over MgSO$_4$, and filtered through a sinter. The solvent from the resulting solution was removed under reduced pressure to give an off-white solid. Trituration with methanol (2×10 cm$^3$) gave a fluffy white solid. The yield was generally found to be in the range 63 to 82%. $^{31}$p{$^1$H} NMR (CD$_2$Cl$_2$) δ=50 ppm.

Example 7

Preparation of (2-trifluoromethylphenyl)$_2$PCH$_2$P(2-trifluoromethylphenyl)$_2$ (2-trifluoromethylphenyl)$_2$PCH$_2$P(2-trifluoromethylphenyl)$_2$ was prepared by following a similar procedure to that described in Example 6 only with the following differences: 2-trifluoromethylphenyl lithium (32 mmol, which was freshly prepared by addition of n-BuLi to 2-trifluoromethylbromobenzene) was used in place of 2-isopropylphenyl lithium. The yield was generally found to be in the range 60 to 80%.

$^{31}$P{$^1$H} NMR (CD$_2$Cl$_2$) δ=−31 ppm.

Example 8

Preparation of (2,4,6-trimethylphenyl)$_2$PCH$_2$P(2,4,6-trimethylphenyl)$_2$ (2,4,6-trimethylphenyl)$_2$PCH$_2$P(2,4,6-trimethylphenyl)$_2$ was prepared by following a similar procedure to that described in Example 6 only with the following differences: 2,4,6-trimethylphenyl lithium (32 mmol, which was freshly prepared by addition of n-BuLi to 2,4,6-trimethylphenylmagnesiumbromide) was used in place of 2-isopropylphenyl lithium. The yield was generally found to be in the range 40 to 70%.

$^{31}$P{$^1$H} NMR (CD$_2$Cl$_2$) δ=−31.5 ppm

Example 9

Preparation of (1-naphthyl)$_2$PCH$_2$P(1-naphthyl)$_2$ (1-naphthyl)$_2$PCH$_2$P(1-naphthyl)$_2$ was prepared by following a similar procedure to that described in Example 6 only with the following differences: 1-naphthyl lithium (32 mmol, which was freshly prepared by addition of n-BuLi to 1-bromonaphthylene) was used in place of 2-isopropylphenyl lithium. The yield was generally found to be in the range 40 to 70%. $^{31}$P{$^1$H} NMR (CD$_2$Cl$_2$) δ=−46.5 ppm.

Example 10

Preparation of [(2-isopropylphenyl)$_2$PN(methyl)P(2-isopropylphenyl)$_2$]NiBr$_2$ The mesityl PNP ligand prepared in Example 1 (565 g/mole; 283 mg; 0.5 mmol) and NiBr$_2$.DME (309 g/mole; 155 mg; 0.5 mmol) were weighed into a Schlenk tube and dry dichloromethane (40 mL) was added. A deep purple solution was formed and the reaction was stirred at room temperature overnight. The solvent was removed under vacuum and the purple oily solid was washed with pentane (2×10 mL). The resulting purple powder (320 mg, 82%) was dried under vacuum, $^{31}$P NMR analysis showed a single signal at δ 45 ppm.

Example 11

Preparation of [(2,4,6-trimethylphenyl)$_2$PN(methyl)P(2,4,6-trimethylphenyl)$_2$]NiBr$_2$ The crude mesityl PNP ligand prepared in Example 5 (27 mg) and NiBr$_2$.DME (309 g/mole; 13 mg; 0.042 mmol) were weighed into a Schlenk tube and dry dichloromethane (10 mL) was added. The stirred mixture was heated to 40° C. for 10 minutes and a purple solution was formed. The reaction was cooled to room temperature and stirred for a further 2 hours. The reaction was filtered to remove insolubles, and the filtrate was evaporated. The purple oily residue was washed with hexane (2×20 mL). The resulting purple powder was dried under vacuum. $^{31}$P NMR analysis showed a single sharp signal at δ 40.4 ppm which was consistent with the desired complex.

Polymerisations

Example 12

Cold (−78° C.) toluene (50 ml) was added to a Schlenk vessel charged with (2-isopropylphenyl)$_2$PN(methyl)P(2-isopropylphenyl)$_2$ as prepared in Example 1 (5.5 mg, 0.01 mmol), nickel bis(1,5-cyclooctadiene) (2.8 mg, 0.01 mmol) and H$^+$(OEt$_2$)[(bis-3,5-trifluoromethyl)phenyl]borate (10.3 mg, 0.01 mmol). This solution was stirred for 15 minutes during which time it was allowed to warm to 0° C. The solution was then degassed under reduced pressure and the Schlenk vessel was then back-filled with an atmosphere of ethylene. The polymerisation was run for 1 hour at ambient temperature during which time the catalyst solution was stirred vigorously and left open to a supply of ethylene at 1 bar pressure. The run was terminated by the addition of dilute aqueous HCl, and the resultant polymer isolated by filtration, washed with acetone and dried in vacuo to yield a white powder. The mass of polyethylene recovered was 1.0 g. The activity of the catalyst was 100 g/mmol.h. The molecular weight of the polymer was Mw (weight average molecular weight)=120000, Mn (number average molecular weight)=32000, PDI (polydispersity index)=3.7. The number of branches in the polymer was (branches per 1000 carbons) methyl=2.2, ethyl=0.2, longer than ethyl=0.3.

Example 13

A polymerisation was performed in substantially the same way as Example 12 only (2-ethylphenyl)$_2$PN(Me)P(2-ethylphenyl)$_2$ (0.01 mmol) as prepared in Example 2 was used instead of (2-isopropylphenyl)$_2$PN(Me)P(2-isopropylphenyl)$_2$. The mass of polyethylene recovered was 0.5 g. The molecular weight of the polymer was Mw=9000, Mn=4000, PDI=2.2. The number of branches in the polymer was (branches per 1000 carbons) methyl=8.5, ethyl=1.1, longer than ethyl=1.9.

Example 14

A polymerisation was performed in substantially the same way as Example 12 only (2-methylphenyl)$_2$PN(Me)P(2-methylphenyl)$_2$ (0.01 mmol) as prepared in Example 3 was used instead of (2-isopropylphenyl)$_2$PN(Me)P(2-isopropylphenyl)$_2$. The mass of polyethylene recovered was 0.6 g. The molecular weight of the polymer was Mw=23000, Mn=9000, PDI=2.5. The number of branches in the polymer was (branches per 1000 carbons) methyl=7.7.

Example 15

A polymerisation was performed in substantially the same way as Example 12 only (2-isopropylphenyl)$_2$PCH$_2$P(2-isopropylphenyl)$_2$ (0.01 mmol) as prepared in Example 6 was used instead of (2-isopropylphenyl)$_2$PN(Me)P(2-isopropylphenyl)$_2$ and after termination by the addition of dilute aqueous HCl, the organic fraction was isolated and toluene removed under reduced pressure to yield polyethylene as a viscous oil/paste. The mass of polyethylene recovered was 0.9 g. The activity of the catalyst was 90 g/mmol.h. The molecular weight of the polymer was Mw=1500, Mn=1100, PDI=1.4. The number of branches in the polymer was (branches per 1000 carbons) methyl=18.0, ethyl=4.0, longer than ethyl=0.6

Example 16

A polymerisation was performed in substantially the same way as Example 12 only (2-trifluoromethylphenyl)$_2$PCH$_2$P(2-trifluoromethylphenyl)$_2$ (0.01 mmol) as prepared in Example 7 was used instead of (2-isopropylphenyl)$_2$PN(Me)P(2-isopropylphenyl)$_2$ and after termination by the addition of dilute aqueous HCl, the organic fraction was isolated and toluene removed under reduced pressure to yield polyethylene as a viscous oil/paste. The mass of polyethylene recovered was 1.2 g. The activity of the catalyst was 120 g/mmol.h The molecular weight of the polymer was Mw=1900, Mn=500, PDI=3.8. The number of branches in the polymer was (branches per 1000 carbons) methyl=45.0, ethyl=22.5, longer than ethyl=9.2.

Example 17

A polymerisation was performed in substantially the same way as Example 12 only (2,4,6-trimethylphenyl)$_2$PCH$_2$P(2,4,6-trimethylphenyl)$_2$ (0.01 mmol) as prepared in Example 8 was used instead of (2-isopropylphenyl)$_2$PN(Me)P(2-isopropylphenyl)$_2$. The mass of polyethylene recovered was 0.4 g. The molecular weight of the polymer was Mw=686000, Mn=148000, PDI=4.8.

Example 18

A polymerisation was performed in substantially the same way as Example 12 only (1-naphthyl)$_2$PCH$_2$P(1-naphthyl)$_2$ (0.01 mmol) as prepared in Example 9 was used instead of (2-isopropylphenyl)$_2$PN(Me)P(2-isopropylphenyl)$_2$ and after termination by the addition of dilute aqueous HCl, the organic fraction was isolated and toluene removed under reduced pressure to yield polyethylene as a viscous oil/paste. The mass of polyethylene recovered was 0.2 g. The molecular weight of the polymer was Mw=9500, Mn=1900, PDI=5.1. The number of branches in the polymer was (branches per 1000 carbons) methyl=19.0.

Example 19

A polymerisation was performed in substantially the same way as Example 12 only 1-hexene (5 ml) was added at the beginning of the polymerisation. The mass of ethylene/hexene copolymer recovered was 0.5 g. The number of branches in the polymer was (branches per 1000 carbons) methyl=2.0, butyl=5.7.

Example 20

Toluene (50 ml) was added to a Schlenk vessel charged with (2-isopropylphenyl)$_2$PN(methyl)P(2-isopropylphenyl)$_2$ as prepared in Example 1 (5.5 mg, 0.01 mmol) and nickel bis(acetylacetonate) (2.6 mg, 0.01 mmol). This solution was stirred for 10 minutes at ambient temperature and then a toluene solution of methylalumoxane (MAO) was added via syringe (1.4 ml, 10% w/w solution in toluene, 2.0 mmol, 200 equivalents). The solution was then degassed under reduced pressure and the Schlenk vessel was then back-filled with an atmosphere of ethylene. The polymerisation was run for 30 minutes at ambient temperature during which time the catalyst solution was stirred vigorously and left open to a supply of ethylene at 1 bar pressure. The run was terminated by the addition of dilute aqueous HCl, and the resultant polymer isolated by filtration, washed with acetone and dried in vacuo to yield a white powder. The mass of polyethylene recovered was 4.1 g. The activity of the catalyst was 820 g/mmol.h. The molecular weight of the polymer was Mw=98000, Mn=40000, PDI=2.4. The number of branches in the polymer was (branches per 1000 carbons) methyl=1.3, ethyl=1.8, longer than ethyl=0.7.

Example 21

A polymerisation was performed in substantially the same way as Example 20 only [(isobutyl)$_2$AlO]$_2$ (2.0 mmol) was used instead of MAO. A small amount of polyethylene was recovered.

Example 22

A polymerisation was performed in substantially the same way as Example 20 only modified-MAO (2.0 mmol) was used instead of MAO. A small amount of polyethylene was recovered.

Example 23

Toluene (50 ml) was added to a Schlenk vessel charged with [(2-isopropylphenyl)$_2$PN(methyl)P(2-isopropylphenyl)$_2$]NiBr$_2$ as prepared in Example 1 (8.0 mg, 0.01 mmol). A toluene solution of methylalumoxane (MAO) was then added via syringe (1.4 ml, 10% w/w solution in toluene, 2.0 mmol, 200 equivalents). The solution was then degassed under reduced pressure and the Schlenk vessel was then back-filled with an atmosphere of ethylene. The polymerisation was run for 30 minutes at ambient temperature during which time the catalyst solution was stirred vigorously and left open to a supply of ethylene at 1 bar pressure. The run was terminated by the addition of dilute aqueous HCl, and the resultant polymer isolated by filtration, washed with acetone and dried in vacuo to yield a white powder. The mass of polyethylene recovered was 3.0 g. The activity of the catalyst was 600 g/mmol.h.

Examples 24

Toluene (10 ml) was added to a Schlenk vessel charged with (2-isopropylphenyl)$_2$PN(methyl)P(2-isopropylphenyl)$_2$ as prepared in Example 1 (5.5 mg, 0.01 mmol) and nickel bis(acetylacetonate) (2.6 mg, 0.01 mmol). This solution was stirred for 10 minutes at ambient temperature and then a toluene solution of methylalumoxane (MAO) was added via syringe (1.4 ml, 10% w/w solution in toluene, 2.0 mmol, 200 equivalents). This solution was then injected into a 500 ml stainless steel autoclave which was previously pressurised to 8 barg ethylene and heated to 50° C., and contained isobutane as diluent. The polymerisation was run for 1 hour during which time ethylene was fed on demand and temperature was maintained at 50° C. The run was terminated by venting of volatiles and the resultant polymer washed with dilute aqueous HCl and acetone and dried in vacuo. The mass of polyethylene recovered was 22.3 g. The molecular weight of the polymer was Mw=65000, Mn=17000, PDI=3.8. The number of branches in the polymer was (branches per 1000 carbons) methyl=1.5, ethyl=0.3, longer than ethyl=0.4.

Supported Catalyst Preparations

Preparation of MAO on ES70X

Toluene (200 mL) was added to a vessel containing silica (ES70X grade, calcined at 200° C. overnight, 20.5 g after calcination) under an inert atmosphere. The slurry was mechanically stirred and MAO (1.5 M, 62.1 mmol, 41.4 mL) was added via syringe. The mixture was stirred for 1 hour at 80° C. before removing excess toluene and drying under vacuum to obtain 15% w/w MAO on silica in quantitative yield.

Example 25 supported [(2-isopropylphenyl)$_2$PN(methyl)P(2-isopropylphenyl)$_2$]Nickel complexes Method A—[(2-isopropylphenyl)$_2$PN(methyl)P(2-isopropylphenyl)$_2$]Ni(Br)$_2$:

The PNP nickel complex prepared in Example 10 (40 μmol) was mixed with MAO/ES70X silica (1.0 g, prepared as described above, 15% w/w MAO on silica) and toluene (20 mL) was added. The mixture was shaken thoroughly and the solid particles were allowed to settle forming an orange-coloured solid beneath the colourless toluene supernatant. The supported catalyst slurry was used directly in subsequent polymerisation examples (See Table 1).

Method B—[(2-isopropylphenyl)$_2$PN(methyl)P(2-isopropylphenyl)$_2$]Ni(acac)$_2$ (acac=acetylacetonate):

The PNP ligand prepared in Example 1 (40 μmol, 23 mg) was mixed with Ni(acac)$_2$ (40 μmol, 10.4 mg) and toluene (20 mL) was added. The mixture was heated briefly to about 50° C. and a purple-coloured solution was formed. MAO/ES70X silica (1.0 g, prepared as described above, 15% w/w MAO on silica) was added. The mixture was shaken thoroughly and the solid particles were allowed to settle forming an orange-coloured solid beneath a colourless toluene supernatant. The supported catalyst slurry was used directly in subsequent polymerisation examples (See Table 1).

Example 26 supported [(2-ethylphenyl)$_2$PN(methyl)P(2-ethylphenyl)$_2$]Ni(acac)$_2$ (acac=acetylacetonate)

The PNP ligand prepared in Example 2 (40 μmol, 20.4 mg) was mixed with Ni(acac)$_2$ (40 μmol, 10.4 mg) and toluene (20 mL) was added. The mixture was heated briefly to about 50° C. and a purple-coloured solution was formed. MAO/ES70X silica (1.0 g, prepared as described above, 15% w/w MAO on silica) was added. The mixture was shaken thoroughly and the solid particles were allowed to settle forming an orange-coloured solid beneath a colourless toluene supernatant. The supported catalyst slurry was used directly in subsequent polymerisation examples (See Table 1).

Example 27 supported [(2-methylphenyl)$_2$PN(methyl)P(2-methylphenyl)$_2$]Ni(acac)$_2$ (acac=acetylacetonate)

The PNP ligand prepared in Example 3 (40 μmol, 18 mg) was mixed with Ni(acac)$_2$ (40 μmol, 10.4 mg) and toluene (20 mL) was added. The mixture was heated briefly to about 50° C. and a colourless solution was formed. MAO/ES70X silica (1.0 g, prepared as described above, 15% w/w MAO on silica) was added. The mixture was shaken thoroughly and the solid particles were allowed to settle forming an orange-coloured solid beneath a colourless toluene supernatent. The supported catalyst slurry was used directly in subsequent polymerisation examples (See Table 1).

Example 28 supported [(2-methoxyphenyl)$_2$PN(methyl)P(2-methoxyphenyl)$_2$]Ni(acac)$_2$ (acac=acetylacetonate)

The PNP ligand prepared in Example 4 (40 μmol, 21 mg) was mixed with Ni(acac)$_2$ (40 μmol, 10.4 mg) and toluene (20 mL) was added. The mixture was heated briefly to about 50° C. and a purple-coloured solution was formed. MAO/ES70X silica (1.0 g, prepared as described above, 15% w/w MAO on silica) was added. The mixture was shaken thoroughly and the solid particles were allowed to settle forming an orange-coloured solid beneath a colourless toluene supernatent. The supported catalyst slurry was used directly in subsequent polymerisation examples (See Table 1).

Example 29 supported [(2,4,6-trimethylphenyl)$_2$PN(methyl)P(2,4,6-trimethylphenyl)$_2$]Ni(Br)$_2$ The PNP nickel complex prepared in Example 11 (785 g/mol, 54 μmol, 42 mg) was mixed with MAO/ES70X silica (1.0 g, prepared as described above, 15% w/w MAO on silica) and toluene (20 mL) was added. The mixture was shaken thoroughly and the solid particles were allowed to settle forming an orange-coloured solid beneath the colourless toluene supernatent. The supported catalyst slurry was used directly in subsequent polymerisation examples (See Table 1).

Supported Polymerisations

Examples 30–35

Supported Catalyst System Homopolymerisation

Results for Examples 30–35 are presented in Table 1. A general procedure for supported homopolymerisations is given as follows:

The reactor (IL) was heated under flowing nitrogen for 1 hour at 90° C. before being cooled to 30° C. Isobutane solvent (500 mL) was added. The reactor was sealed and heated to 50° C.; ethylene was admitted such that the total pressure was increased by 8 bar. In a separate vessel, a slurry of supported catalyst in toluene (prepared according to the relevent Example as described in Table 1 containing 40 μmol Ni was shaken and injected directly into the reactor under pressure. The reaction was allowed to proceed for the time described in Table 1 before terminating the polymerisation by shutting off the ethylene supply and venting the reactor pressure. Recovered polymer was dried overnight under vacuum, before weighing and submitting for analysis.

TABLE 1

Examples 30–35: ethylene homo-polymerisation

| Example | Complex Example No. | Time min | Activity g/mmol.h | Mw | Mn | PD | Branches/1000 C. |
|---|---|---|---|---|---|---|---|
| 30 | 25A | 60 | 210 | 62000 | 2700 | 23 | 6.5 |
| 31 | 25B | 70 | 225 | 73000 | 7300 | 10 | 1.8 |
| 32 | 26 | 95 | 24 | 96000 | 700 | 143 | 28.1 |
| 33 | 27 | 80 | 7 | 55000 | 400 | 143 | 47.1 |
| 34 | 28 | 60 | 143 | 177000 | 2500 | 70 | 4.6 |
| 35 | 29 | 60 | 2 | 363000 | — | — | — |

Example 36

Supported Catalyst System, Copolymerisation with Hexene

The reactor (IL) was heated under flowing nitrogen for 1 hour at 90° C. before being cooled to 30° C. The reactor was charged hex-1-ene (125 mL) and isobutene (375 mL). The reactor was sealed and after heating to 50° C., ethylene was admitted such that the total pressure was increased by 4 bar. In a separate vessel, a slurry of supported catalyst in toluene (prepared according to Example 25B) containing 40 μmol Ni was shaken and injected directly into the reactor under pressure The ethylene uptake was monitored for 90 min. before terminating the polymerisation by shutting off the ethylene supply and venting the reactor pressure. Recovered polymer was dried overnight under vacuum, before weighing and submitting for analysis. 1.0 g of polyethylene was isolated, giving an average activity of 17 g/mmol.h. $^1$H NMR analysis shows 4 Me branches/1000 C atoms and 11 Bu branches/1000 C.

Example 37

A polymerisation was performed in substantially the same way as Example 12 only 1 bar propylene was used instead of ethylene. A small amount of polypropylene was recovered.

Example 38

A polymerisation was performed in substantially the same way as Example 20 palladium(II) acetate (0.01 mmol) was used instead of nickel bis(acetylacetonate) and a solution of tris(pentafluorophenyl)borane (0.2 mmol, 20 equivalents) in toluene (5 ml) was used instead of MAO. The polymerisation was run for 20 hours. A small amount of polyethylene was recovered.

Example 39

A polymerisation was performed in substantially the same way as Example 12 only the toluene solvent was not dried and degassed prior to use. The mass of polyethylene recovered was 1.0 g.

Example 40

A polymerisation was performed in substantially the same way as Example 12 only water (5 ml) was added at the start of polymerisation and the polymerisation was run for 5 hours. The mass of polyethylene recovered was 0.4 g.

Example 41

A polymerisation was performed in substantially the same way as Example 12 only diethyl ether was used as solvent instead of toluene. The mass of polyethylene recovered was 0.6 g.

Example 42

A polymerisation was performed in substantially the same way as Example 12 only methanol was used as solvent instead of toluene. The mass of polyethylene recovered was 0.4 g Example 43

A polymerisation was performed in substantially the same way as Example 12 only ω-undecylenyl alcohol (5 ml) was added at the start of polymerisation and the polymerisation was run for 15 hours. The mass of ethylene/ω-undecylenyl alcohol copolymer recovered was 0.8 g. The polymer was analysed by NMR spectroscopy which determined 1.9 nonanol branches per 1000 carbons.

I claim:

1. A process for the polymerization of olefins, consisting essentially of contacting a monomer selected from the group consisting of a hydrocarbon olefin, an olefin having a polar functionality and mixtures thereof under polymerization conditions with a polymerization catalyst or catalyst system which includes the components:
   (a) a source of a Group VIII metal;
   (b) a bidentate phosphine ligand having the formula $(R^1)(R^1)P\text{---}X\text{---}P(R^1)(R^1)$, where each $R^1$ is independently a phenyl group or a substituted phenyl group with the proviso that at least one of the $R^1$ groups is a phenyl group having at least one ortho substituent, and X is a bridging group of the structure $\text{---}[N]_x\text{---}[P]_y\text{---}[N]\text{---}$, where x and y are independently 0 or 1, or $\text{---}C(R^4)_2\text{---}$ where each $R^4$ may be the same or different and is hydrogen or a monovalent hydrocarbyl group, a substituted hydrocarbyl group or a heterohydrocarbyl group; and
   (c) optionally a promotor.

2. A process for the polymerization of 1-olefins, comprising:
   (1) preparing a prepolymer-based catalyst by contacting one or more 1-olefins with a polymerization catalyst or catalyst system which includes the components:
   (a) a source of a Group VIII metal;
   (b) a bidentate phosphine ligand having the formula $(R^1)(R^1)P\text{---}X\text{---}P(R^1)(R^1)$, where each $R^1$ is independently a phenyl group or a substituted phenyl group with the proviso that at least one of the $R^1$ groups is a phenyl group having at least one ortho substituent, and X is a bridging group of the structure $\text{---}[N]_x\text{---}[P]_y\text{---}[N]\text{---}$, where x and y are independently 0 or 1, or $\text{---}C(R^4)_2\text{---}$ where each $R^4$ may be the same or different and is hydrogen or a monovalent hydrocarbyl group, a substituted hydrocarbyl group or a heterohydrocarbyl group; and
   (c) optionally a promotor; and
   (2) contacting the prepolymer-based catalyst with one or more 1-olefins.

3. Process according to claim 1 or 2 wherein the Group VIII metal is iron, cobalt, nickel or palladium.

4. Process according to claim 1 or 2 wherein component (a) is an inorganic or organic salt, or an organometallic or coordination complex.

5. Process according to claim 1 or 2 wherein component (b) is a compound of the formula (I)

$$(R^1)(R^1)P-(NR^2)_x-(PR^3)_{y-NR}{}^2-P(R^1)(R^1) \qquad (I)$$

wherein each $R^2$ is the same or different, and $R^2$ and $R^3$ are each independently hydrogen or a monovalent hydrocarbyl group, a substituted hydrocarbyl group or a hetero-hydrocarbyl group, and x and y are independently 0 or 1.

6. Process according to claim 5 wherein $R^2$ and $R^3$ are each independently hydrogen, methyl, ethyl, isopropyl, n-butyl, t-butyl, n-hexyl, cyclohexyl, phenyl, tolyl, trifluoromethyl, methoxymethyl, anisyl, phenol, methoxy, phenoxy, dimethylamino, diethylamino, methylphenoxy or methoxyphenoxy.

7. Process according to claim 5 wherein x and y are both zero.

8. Process according to claim 1 or 2 wherein component (b) is a compound of formula (II):

$$(R^1)(R^1)P-C(R^4)(R^4)-P(R^1)(R^1) \qquad (II)$$

wherein each $R^4$ may be the same or different and is hydrogen or a monovalent hydrocarbyl group, a substituted hydrocarbyl group or a hetero-hydrocarbyl group.

9. Process according to claim 8 wherein each $R^4$ is independently hydrogen or a $C_1$ to $C_6$ alkyl or aryl group, or the $R^4$ groups are linked to form a cyclic structure.

10. Process according claim 1 or 2 wherein the substituted phenyl group is a phenyl group substituted with a halide, a hydrocarbyl group, a substituted hydrocarbyl group or a heterohydrocarbyl group.

11. Process according to claim 10 wherein each $R^1$ group is a substituted phenyl group having at least one halide, hydrocarbyl, substituted hydrocarbyl or heterohydrocarbyl substituent in the ortho position.

12. Process according to claim 10 wherein each of the $R^1$ groups is a substituted phenyl group having at least one ortho hydrocarbyl, alkoxy, amido or perfluoronated substituent, or two adjacent substituents are joined to form a —$C_4H_4$— unit so as to form part of a benzene ring.

13. Process according to claim 1 or 2 wherein component (b) is:
(2-methylphenyl)(phenyl)PN(methyl)P(phenyl)$_2$;
(2-methylphenyl)$_2$PN(methyl)P(phenyl)$_2$;
(2-methylphenyl)(phenyl)PN(methyl)P(2-methylphenyl)(phenyl);
(2-methylphenyl)$_2$PN(methyl)P(2-methylphenyl)$_2$;
(2-ethylphenyl)$_2$PN(methyl)P(2-ethylphenyl)$_2$;
(2-isopropylphenyl)$_2$PN(methyl)P(2-isopropylphenyl)$_2$;
(2,3-dimethylphenyl)$_2$PN(methyl)P(2,3-dimethylphenyl)$_2$;
(2,4-dimethylphenyl)$_2$PN(methyl)P(2,4-dimethylphenyl)$_2$;
(2,6-dimethylphenyl)$_2$PN(methyl)P(2,6-dimethylphenyl)$_2$;
(2-methyl-6-isopropylphenyl)$_2$PN(methyl)P(2-methyl-6-isopropylphenyl)$_2$;
(2,6-diisopropylphenyl)$_2$PN(methyl)P(2,6-diisopropylphenyl)$_2$;
(2,4,6-trimethylphenyl)$_2$PN(methyl)P(2,4,6-trimethylphenyl)$_2$;
(2-tertbutylphenyl)$_2$PN(methyl)P(2-tertbutylphenyl)$_2$;
(2-methoxyphenyl)$_2$PN(methyl)P(2-methoxyphenyl)$_2$;
(2-trifluoromethylphenyl)$_2$PN(methyl)P(2-trifluoromethylphenyl)$_2$;
(2-phenylphenyl)$_2$PN(methyl)P(2-phenylphenyl)$_2$;
(1-naphthyl)$_2$PN(methyl)P(1-naphthyl)$_2$;
(2-isopropylphenyl)$_2$PN(butyl)P(2-isopropylphenyl)$_2$;
(2-isopropylphenyl)$_2$PN(phenyl)P(2-isopropylphenyl)$_2$;
(2-isopropylphenyl)$_2$PN(methyl)N(methyl)P(2-isopropylphenyl)$_2$;
(2-isopropylphenyl)$_2$PN(methyl)P(Ph)N(methyl)P(2-isopropylphenyl)$_2$;
(2-methylphenyl)(phenyl)PCH$_2$P(phenyl)$_2$;
(2-methylphenyl)$_2$PCH$_2$P(phenyl)$_2$;
(2-methylphenyl)(phenyl)PCH$_2$P(2-methylphenyl)(phenyl);
(2-methylphenyl)$_2$PCH$_2$P(2-methylphenyl)$_2$;
(2-ethylphenyl)$_2$PCH$_2$P(2-ethylphenyl)$_2$;
(2-isopropylphenyl)$_2$PCH$_2$P(2-isopropylphenyl)$_2$;
(2,3-dimethylphenyl)$_2$PCH$_2$P(2,3-dimethylphenyl)$_2$;
(2,4-dimethylphenyl)$_2$PCH$_2$P(2,4-dimethylphenyl)$_2$;
(2,6-dimethylphenyl)$_2$PCH$_2$P(2,6-dimethylphenyl)$_2$;
(2-methyl-6-isopropylphenyl)$_2$PCH$_2$P(2-methyl-6-isopropylphenyl)$_2$;
(2,6-diisopropylphenyl)$_2$PCH$_2$P(2,6-diisopropylphenyl)$_2$;
(2,4,6-trimethylphenyl)$_2$PCH$_2$P(2,4,6-trimethylphenyl)$_2$;
(2-tertbutylphenyl)$_2$PCH$_2$P(2-tertbutylphenyl)$_2$;
(2-methoxyphenyl)$_2$PCH$_2$P(2-methoxyphenyl)$_2$;
(2-trifluoromethylphenyl)$_2$PCH$_2$P(2-trifluoromethylphenyl)$_2$;
(2-phenylphenyl)$_2$PCH$_2$P(2-phenylphenyl)$_2$;
(1-naphthyl)$_2$PCH$_2$P(1-naphthyl)$_2$;
(2-isopropylphenyl)$_2$PC(phenyl)$_2$P(2-Isopropylphenyl)$_2$; or
(2-isopropylphenyl)$_2$PC(methyl)$_2$P(2-isopropylphenyl)$_2$.

14. Process according to claim 1 or 2 wherein component (c) is an organoaluminium compound, a organoboron compound, or a salt of a cationic oxidising agent and a non-coordinating compatible anion.

15. Process according to claim 1 or 2 wherein component (c) is an alumoxane.

16. Process according to claim 9 wherein the $C_1$ to $C_6$ alkyl or aryl group is a methyl, ethyl or phenyl group.

17. Process according to claim 12, wherein the substituent is a methyl, ethyl, iso-propyl, tert-butyl, phenyl, methoxy, ethoxy, phenoxy, dimethylamido, diethylamido, trifluoromethyl, perfluoroethyl or pentafluorophenyl substituent.

18. A process for the polymerization of olefins, consisting essentially of contacting a monomer selected from the group consisting of a hydrocarbon olefin, an olefin having a polar functionality and mixtures thereof under polymerization conditions with a polymerization catalyst or catalyst system which includes:

(i) a compound of the formula (III)

$$[(L)_p(L^1)_q M^m(Q)](A^n)_{(m-p)/n} \qquad (III); \text{ and}$$

(ii) optionally a promoter, wherein M is a Group VIII metal in formal oxidation state m, each L is independently a monoanionic group or ligand, $L^1$ is independently a neutral group or ligand, each A is independently a weakly coordinating or non-coordinating anion with a formal negative charge of n, p may have any value between 0 and m, q is an integer between 0 and 4 and Q is a bidentate phosphine ligand having the formula $(R^1)(R^1)P-X-P(R^1)(R^1)$, where each $R^1$ is independently a phenyl group or a substituted phenyl group with the proviso that at least one of the $R^1$ groups is a phenyl group having at least one ortho substituent, and X is a bridging group of the structure —[N]$_x$—[P]$_y$—[N]—, where x and y are independently 0 or 1, or —C(R$^4$)$_2$— where each R$^4$ may be the same or different and is hydrogen or a monovalent hydrocarbyl group, a substituted hydrocarbyl group or a hetero-hydrocarbyl group.

19. Process according to claim 18 wherein L is halide, acetate, acetyl acetonate, alkyl, heteroalkyl, allyl, or hydride, L$^1$ is an olefin, carbon monoxide, a phosphine or a solvent molecule and A is BF$_4$$^-$, SbF$_6$$^-$, PF$_6$$^-$, triflate, aryl or alkyl borate, sulfate or phosphate.

20. Process according to claim 18 wherein M is nickel, and the values of p, q and m are p=0, q=2 and m=0; p=1, q=1 and m=2; p=2, q=0 and m=2; or p=0, q=2 and m=2.

21. Process according to claim 1 or 18 wherein the hydrocarbon olefin is ethylene, propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, styrene, 2-butene, cyclohexene, norbornene, butadiene, or 1,5-hexadiene and the olefin having a polar functionality is methyl methacrylate, methyl acrylate, butyl acrylate, acrylonitrile, vinyl acetate, 2-vinyl-1,3-dioxolane, methyl 3-butenoate, methyl 4-pentenoate, ω-undecylenyl alcohol, ethyl undecylenate, undecylenoic acid, or functionaliized norbornenes.

22. Process according to claim 1, 2 or 18 wherein the polymerization catalyst or catalyst system is supported on a support material which includes silica, alumina, MgCl$_2$, zirconia, polyethylene, polypropylene, polystyrene, or poly(aminostyrene).

23. Process according to claim 1, 2 or 18 which is conducted in gas phase, slurry phase, bulk phase or solution phase.

* * * * *